United States Patent
Zlobinsky

(10) Patent No.: US 8,496,564 B2
(45) Date of Patent: Jul. 30, 2013

(54) SYSTEM AND METHOD FOR SUPERVISED HOME CARE REHABILITATION OF STROKE SURVIVORS

(76) Inventor: Rachel Zlobinsky, Kiryat Tivon (IL)

( * ) Notice: Subject to any disclaimer, the term of this patent is extended or adjusted under 35 U.S.C. 154(b) by 0 days.

(21) Appl. No.: 13/388,453

(22) PCT Filed: Aug. 1, 2010

(86) PCT No.: PCT/IL2010/000619
§ 371 (c)(1),
(2), (4) Date: Feb. 8, 2012

(87) PCT Pub. No.: WO2011/016024
PCT Pub. Date: Feb. 10, 2011

(65) Prior Publication Data
US 2012/0129655 A1    May 24, 2012

Related U.S. Application Data

(63) Continuation of application No. 12/534,870, filed on Aug. 4, 2009, now abandoned.

(51) Int. Cl.
A63B 24/00    (2006.01)
(52) U.S. Cl.
USPC .................. 482/9; 482/1; 482/8; 482/901
(58) Field of Classification Search
USPC .......................................... 482/1–9, 900–902
See application file for complete search history.

(56) References Cited

U.S. PATENT DOCUMENTS

| | | |
|---|---|---|
| 3,572,700 A | 3/1971 | Mastropaolo et al. |
| 4,186,920 A | 2/1980 | Flore et al. |
| 4,423,630 A | 1/1984 | Morrison |
| 4,436,097 A | 3/1984 | Cummingham |
| 4,463,764 A | 8/1984 | Anderson et al. |
| 4,911,425 A | 3/1990 | Kynast et al. |
| 5,207,623 A | 5/1993 | Tkatchouk et al. |
| 5,277,685 A | 1/1994 | Gonzales |
| 5,318,487 A | 6/1994 | Golen et al. |
| 5,324,060 A | 6/1994 | Van Vooren et al. |
| 5,410,472 A | 4/1995 | Anderson |
| 5,423,563 A | 6/1995 | Wild |
| 5,476,429 A | 12/1995 | Bigelow et al. |
| 5,746,684 A | 5/1998 | Jordan |
| 5,941,837 A | 8/1999 | Amano et al. |
| 6,142,911 A | 11/2000 | Sauvignet et al. |
| 6,206,837 B1 | 3/2001 | Brugnoli |
| 6,736,759 B1 | 5/2004 | Stubbs et al. |
| 7,004,885 B1 | 2/2006 | Wu et al. |
| 7,011,605 B2 | 3/2006 | Shields |
| 7,727,116 B2 | 6/2010 | Kaplan et al. |
| 2004/0176226 A1 | 9/2004 | Carlson |
| 2006/0063980 A1 | 3/2006 | Hwang et al. |
| 2006/0094569 A1 | 5/2006 | Day |
| 2006/0199700 A1 | 9/2006 | LaStayo et al. |
| 2006/0229163 A1 | 10/2006 | Waters |
| 2007/0037664 A1 | 2/2007 | Kaplan et al. |
| 2009/0088300 A1 | 4/2009 | Catanescu |

*Primary Examiner* — Glenn Richman

(57) ABSTRACT

A transportable apparatus for performing cardiovascular training, including: an exercise device that is adapted to enable a user to perform a specific motion pattern; an ergometer that provides an indication of the amount of work performed by the user of the exercise device; an alarm system that provides an indication to the user responsive to the readings of the ergometer; wherein the alarm system is preprogrammed to provide indications responsive to one or more readings of the ergometer based on the results of a cardiorespiratory exercise test performed on the user with the exercise device.

21 Claims, 7 Drawing Sheets

| STAGE | ACTS | LOCATION | INVOLVED | NOT INVOLVED |
|---|---|---|---|---|
| 1-ASSEMBLE APPARATUS | 1-MATCH TO PARAMETERS OF THE USER'S WHEELCHAIR<br>2-ATTACH TO WHEELCHAIR | HOME/MEDICAL CENTER BY TECHNICIAN | | • EXERCISE DEVICE<br>• ERGOMETER<br>• ALARM SYSTEM |
| 2-DESIGN MOTION PATTERN | 1-EVALUATION OF NEUROLOGICAL IMPAIRMENT OF THE USER<br>2-GENERATION OF MOTION STEREOTYPE FOR THE PROCESS OF INDIVIDUAL SELF-ACTIVATING EXERCISE TRAINING OF THE USER | HOME/MEDICAL CENTER BY PHYSICAL THERAPISTS | • EXERCISE DEVICE | • EXERCISE DEVICE<br>• ERGOMETER<br>• ALARM SYSTEM |
| 3-PLAN FITNESS PROGRAM | 1-EVALUATION OF CARDIORESPIRATORY FITNESS OF THE USER BY INTEGRATIVE CARDIOPULMONARY EXERCISE TEST<br>2-DEFINITION OF THE OPTIMAL & MAXIMAL PERMISSIBLE LEVEL OF WORK LOADING FOR THE USER | MEDICAL CENTER BY MD | • EXERCISE DEVICE<br>• ERGOMETER | • ALARM SYSTEM |
| 4-PROGRAM APPARATUS BASED ON TEST RESULTS | 1-CALIBRATION OF ALARM SYSTEM UNDER THE MAXIMUM PERMISSIBLE LEVEL OF LOADING FOR THE USER<br>2-LOCK THE ELECTRONIC LOCK | MEDICAL CENTER BY MD | • ALARM SYSTEM | • EXERCISE DEVICE<br>• ERGOMETER |
| 5-USE APPARATUS TO PERFORM SELF CARE REHAB PLAN | 1-PERFORMING OF INDIVIDUAL PROGRAM DURING RECURRENCE OF THIS INDIVIDUAL MOTION STEREOTYPE UNDER THE SUPERVISION OF THE PROGRAMED ALARM SYSTEM | HOME BY USER (SELF CARE) | • EXERCISE DEVICE<br>• ERGOMETER<br>• ALARM SYSTEM | |

FIG. 2B

SYSTEM AND METHOD FOR SUPERVISED HOME CARE REHABILITATION OF STROKE SURVIVORS

RELATED APPLICATIONS

This application claims benefit under 35 USC 371 (c) as being a national phase filing of international application no: PCT/IL10/00619 filed Aug. 1, 2010 and published as WO 2011/016024. The International application claims priority under 35 USC 365(c) as a continuation of U.S. application Ser. No. 12/534,870 filed on Aug. 4, 2009 now abandoned.

FIELD OF THE INVENTION

The present invention relates generally to a system and method for physical rehabilitation to improve cardiorespiratory fitness of people after suffering from a stroke or other ailments and more specifically wherein the rehabilitation is tailored to the cardiovascular ability and needs of the individual.

BACKGROUND OF THE INVENTION

Millions of people around the world have suffered from various degrees of strokes. Stroke remains a leading cause of long term disability in the United States. Approximately 40% of stroke survivors require at least some assistance with ADL (activities of daily living), and at least half of the stroke survivors require at least some assistance. Many of the stroke survivors experience long term effects such as partial paralysis due to permanent neurological deficiencies.

Consequently, stroke survivors are often deconditioned and predisposed to a sedentary lifestyle that limits performance of ADL, and may contribute to the risk of suffering from cardiovascular disease. As with heart disease physical inactivity serves as an emerging risk factor for recurrent stroke. It has been proven that daily caloric expenditure by performing aerobic exercise strongly reduces the risk of suffering from a recurrent stroke. More than 70% of stroke patients suffer from neurological impairment that requires a long term rehabilitation program. The main rehabilitation goals for stroke patients are:
1. Preventing complications from prolonged inactivity;
2. Increasing aerobic fitness;
3. Decreasing recurrent stroke and cardiovascular events.

These goals can be achieved only by using a long term rehabilitation program. The recommended weekly expenditure of energy is approximately 4200 KJ. The recommended frequency of training is between 3 to 7 times a week with a duration of 30 to 60 minutes of continuous or accumulated exercise.

In many cases the stroke survivor fails to perform a long term exercise program to the full extent due to the complexity of getting to a rehabilitation center in the survivors incapacitated state. Such programs are not accessible to most patients due to social and economic reasons. The solution to this problem would require performing a long term rehabilitation program in the patient's home environment without the aid of trained medical personnel.

A home training program requires two important conditions:
1. A high safety level for the patient while performing the exercise;
2. An exercise device located at the home of the patient.

Generally exercise is a normal human function that can be undertaken with a high level of safety by most people including stroke survivors. However stroke survivors are at a higher level of risk when performing exercise. One problem is related to balance wherein stroke survivors tend to be more prone to suffer from falling over and getting hurt. A second problem is sudden cardiac death which may occur if the person is overloaded while performing exercise. Cardiac disease has been reported to occur in up to 75% of stroke survivors, either having occurred before suffering from the stroke or having developed afterwards. Therefore an exercise program for stroke survivors needs to be able to prevent falling over and to prevent work overloading the person's cardiac system. Each person needs an individually designed program that is monitored to prevent work overload.

The exercise device needs to allow the user to perform exercise at home according to a specific program designed for the user. Preferably it should be customizable, portable and non expensive. Additionally, it should enable exploitation of the person's large muscles to maximize effectiveness of the training program and enable people that suffer from various neurological deficits or anatomic limitations to be able to benefit from the exercise device with minimal risk.

SUMMARY OF THE INVENTION

An aspect of an embodiment of the invention, relates to an apparatus and method for assisting in home exercise training with a high level of safety, thus providing accessibility to rehabilitation programs for a wider range of stroke survivors. The apparatus includes an exercise device with an ergometer and an alarm system. The exercises device is transportable by the user or a single person, so that it can be taken to a medical center to be used for performing a cardiopulmonary exercise test for the user and for designing an individual exercise program for the specific user with the device at the user's home. The exercise device is adapted to allow the design of a motion pattern and enable varying the load on the muscles for training and for performing an integrative cardiopulmonary exercise test. Optionally, the motion pattern allows exploitation of the strength of the large muscles, for example the hip and pelvic muscles. In an exemplary embodiment of the invention, the apparatus is attachable to a wheel chair and adapted to enable a person seated in the wheelchair to perform exercise. In an exemplary embodiment of the invention, the exercise device includes parts that move some of the person's limbs responsive to movement of other parts by a different limb of the person, for example the person may perform exercise with a healthy foot causing a damaged foot to move reciprocally.

In some embodiments of the invention, the exercise program may be performed while the wheel chair is stationary. Alternatively, the exercise program may include motion of the wheel chair.

The ergometer provides an indication of the amount of effort performed by the person using the apparatus during training, and also during the integrative cardiopulmonary test. It should be noted that the same ergometer is used in both cases. The ergometer readings serve as the criterion for determining load adequacy during the stage of program designing at the medical center and during exercise training at home. Additionally, the apparatus includes an alarm that gives an indication if the ergometer measures work exceeding a pre-determined amount. Optionally, the alarm prevents the apparatus from allowing the user to continue to perform exercise if exceeding the pre-determined amount.

In an exemplary embodiment of the invention, the apparatus provides the user with an indication regarding the amount of effort exerted by the person during use of the apparatus.

Optional the indication is a visual or audio indication. In some embodiments of the invention, the user may select different levels of difficulty for use of the apparatus, for example wherein at a harder level a person performs the same amount of work in a shorter time than at an easier level. The alarm provides user safety while performing exercise.

In an exemplary embodiment of the invention, the user initially assembles the apparatus at home. Optionally, a physical therapist visits the user and designs a motion pattern for the user to perform with the exercise device. The user then visits the medical center that checks the physical health of the user and designs a fitness program for the user. At the medical center the cardiorespiratory fitness of the user is evaluated by an integrative cardiopulmonary exercise test that determines a safe work load range for the user. During the testing only the motion pattern designed by the physiotherapist is used, but with varying degrees of resistance selected on the exercise device.

In an exemplary embodiment of the invention, the medical center measures the correlation between the user's cardiopulmonary state and the readings of the ergometer. The medical center designs an exercise program for the user, using the motion pattern designed by the physiotherapist. Then the medical center programs the apparatus so that the user will receive warnings when exceeding a recommended stress level. Optionally, above a certain level the apparatus will be programmed to prevent the user from continuing to perform exercise with the apparatus. In some embodiments of the invention, there may be multiple warning levels of increasing severity.

After testing and designing the user takes the apparatus home to start performing the home self acting exercise training Over time the above process is repeated to evaluate the user's progress and adjust the training program to fit the user's state.

In some embodiments of the invention, the apparatus is connected over a communication network (e.g. the Internet) to the medical center, which can then monitor the user and/or apparatus. Optionally, the work progress of the user can be transmitted in real time to the medical center. Additionally, other physiological parameters of the user can be transmitted over the communication connection, for example Holter and ECG data.

There is thus provided according to an exemplary embodiment of the invention, a transportable apparatus for performing cardiovascular training, including:

an exercise device that is adapted to enable a user to perform a specific motion pattern;

an ergometer that provides an indication of the amount of work performed by the user of the exercise device;

an alarm system that provides an indication to the user responsive to the readings of the ergometer;

wherein the alarm system is preprogrammed to provide indications responsive to one or more readings of the ergometer based on the results of a cardiorespiratory exercise test performed on the user with the exercise device.

In an exemplary embodiment of the invention, the exercise device is adapted to be attached to a wheel chair to enable performing exercise while seated in the wheel chair. Optionally, the exercise device is adapted to be activated by the large muscles in the area of the thigh and pelvis. In an exemplary embodiment of the invention, the exercise device is adapted to cause the user's legs to perform reciprocal motion. Optionally, the alarm system provides continuous readings related to the amount of effort performed by the user. In an exemplary embodiment of the invention, the readings are provided as audio signals. Optionally, the readings are provided as visual signals. In an exemplary embodiment of the invention, the level of resistance of the exercise device is adjusted to match the ability of the user, Optionally, the exercise device is calibrated with a different level of resistance on each side of the exercise device. In an exemplary embodiment of the invention, the cardiorespiratory exercise test determines a maximum amount of effort allowed by the user during a single session. Optionally, the alarm system provides signals to remind the user to perform exercise. In an exemplary embodiment of the invention, the alarm system provides signals to notify the user to stop performing exercise. Optionally, the alarm system provides signals to help the user to follow a pre-programmed exercise plan. In an exemplary embodiment of the invention, the alarm system prevents the user from continuing to perform exercise with the exercise device. Optionally, the exercise device is adapted to be used while the wheel chair is stationary. In an exemplary embodiment of the invention, the exercise device is adapted to enable the user to control the motion of the wheel chair. Optionally, the apparatus includes a pump that produces compressed air from the exercise performed by the user. In an exemplary embodiment of the invention, the compressed air is used to move the wheel chair. Optionally, the motion pattern is determined by a physiotherapist examination. In an exemplary embodiment of the invention, the motion pattern is designed to fit the user's neurological or motor deficiency.

There is further proved according to an exemplary embodiment of the invention, a method of performing home based cardiovascular exercise training, including:

assembling an exercise device that is transportable by a single person;

designing a motion pattern to be performed by the user of the exercise device;

adjusting the resistance of the elements of the exercise device based on the physical state of the user and the designed motion pattern;

training the user to use the exercise device;

testing the cardiorespiratory ability of the user while using the exercise device and monitoring the readings of an ergometer that provides indication of the effort of the user while using the device;

planning a fitness program based on the testing;

programming an alarm system of the exercise device to provide the user with indications responsive to various readings of the ergometer while using the exercise device.

In an exemplary embodiment of the invention, the exercise device is adapted to be attached to a wheelchair. Optionally, the method includes warning the user if he exceeds a predetermined exercise rate. In an exemplary embodiment of the invention, the alarm system prevents the user from performing exercise with the exercise device responsive to readings from the ergometer.

BRIEF DESCRIPTION OF THE DRAWINGS

The present invention will be understood and better appreciated from the following detailed description taken in conjunction with the drawings, Identical structures, elements or parts, which appear in more than one figure, are generally labeled with the same or similar number in all the figures in which they appear, wherein:

FIG. 2B is a table of details related to the practice of a method for performing rehabilitation exercise, according to an exemplary embodiment of the invention;

DETAILED DESCRIPTION

Figure 1:
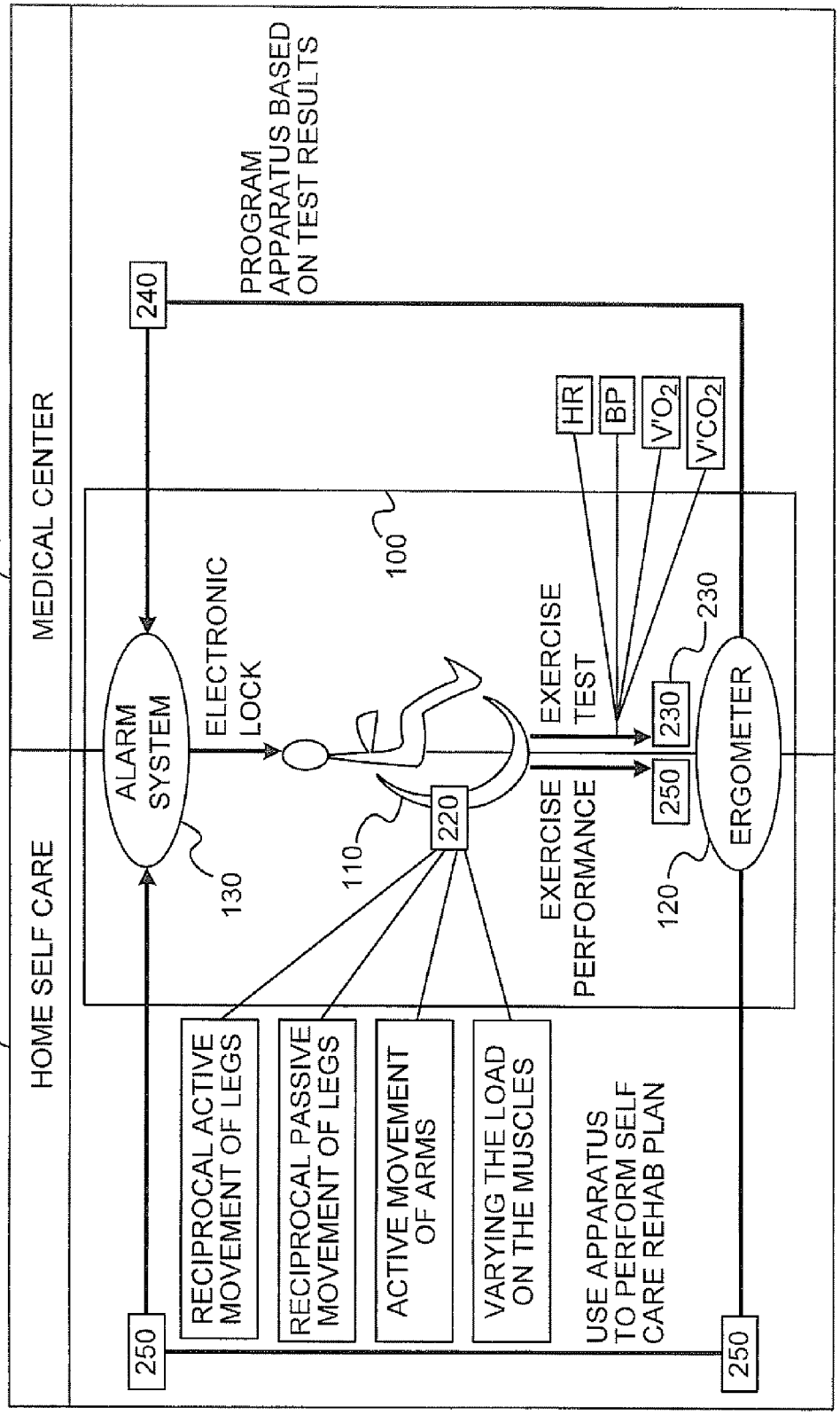
FIG. 1 is a schematic illustration of a system for performing rehabilitation exercise, according to an exemplary embodiment of the invention.

FIG. 1 is a schematic illustration of an apparatus 100 for performing rehabilitation exercise, according to an exemplary embodiment of the invention. Apparatus 100 is based on the use of an exercise device 110 that is coupled to an ergometer 120 and an alarm system 130. Apparatus 100 is portable and can be used by a person at home 140 for safe self training. Additionally, it can also be transported by the user or a single person to a medical center 150 for conducting evaluation of the user while using exercise device 110 and designing an exercise program that fits the condition of the user.

Figure 2A:
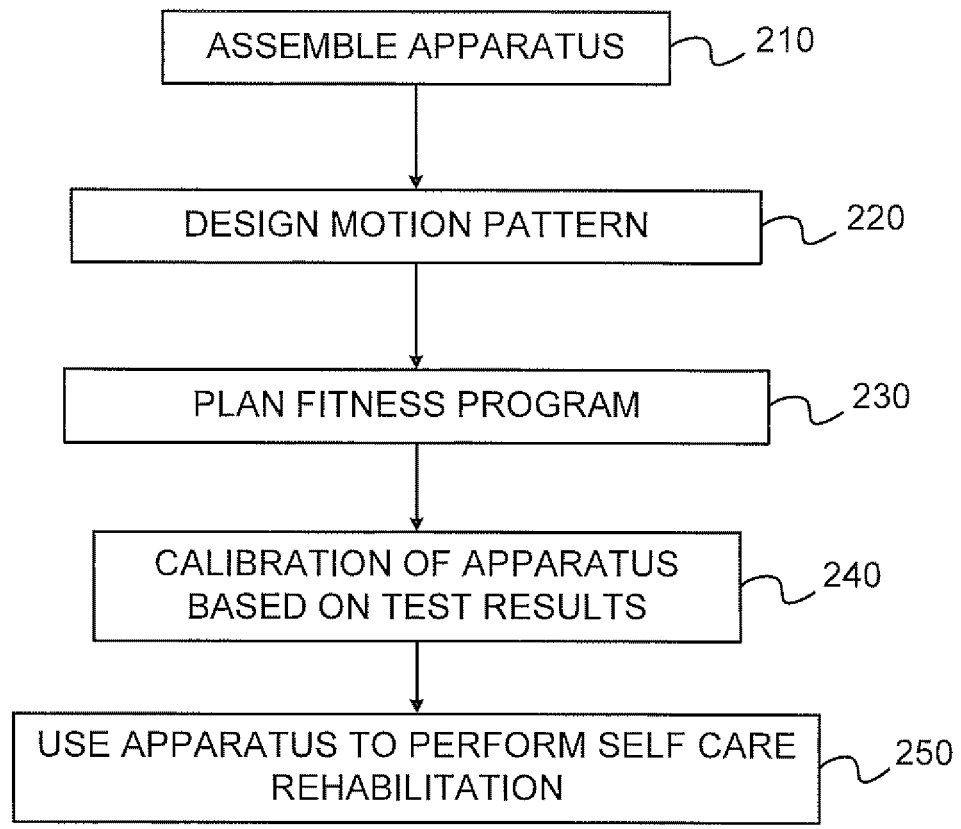
FIG. 2A is a flow diagram of a method of using a system for performing rehabilitation exercise, according to an exemplary embodiment of the invention.

FIG. 2A is a flow diagram of a method 200 of using apparatus 100 for performing rehabilitation exercise, according to an exemplary embodiment of the invention. In an exemplary embodiment of the invention, apparatus 100 is made up from a wheel chair that provides portability of the stroke victim, and a mechanism that is attached to the wheel chair, providing together functionality as an exercise device 110. Optionally, other types of exercise devices 110 may be used, for example rowing machines or other devices as long as the user is able to cope with them despite specific impairments and that they can be coupled to the other required elements (e.g. alarm system 130 and ergometer 120). Optionally, an exercise device 110 that includes a chair may be used for example for stroke victims that are capable of walking on their own. Using a wheelchair as part of exercise device 110 provides enhanced portability since the user may use it for everyday transportation in addition to performing exercise. The use of a wheel chair or chair as part of exercise device 110 is preferential for home training, since it prevents musculoskeletal injury from falling down.

FIG. 2B is a table of details 290 related to the practice of method 200 for performing rehabilitation exercise, according to an exemplary embodiment of the invention.

In the first stage apparatus 100 is assembled (210) by connecting it to the user's wheel chair to form an exercise device 110 coupled to an ergometer 120 and an alarm system 130. Optionally, a technician may visit the user at home to assemble apparatus 100 onto the user's wheelchair, or alternatively the user may visit medical center 150 and have it assembled there. In some embodiments of the invention, the parts provided for exercise device 110 are designed for specific models of wheel chairs. Optionally, multiple versions of parts for exercise device 110 may be manufactured to match the various models of wheel chairs in the market, and form similar functioning exercise devices 110.

In an exemplary embodiment of the invention, after assembling apparatus 100 a physiotherapist examines the user and designs a motion pattern (220) based on the state of its user. The motion pattern will serve the user in exercising with exercise device 110 and while being tested at the medical center.

In an exemplary embodiment of the invention, the physiotherapist visits the user at home. At this stage only exercise device 110 is used from apparatus 100, whereas ergometer 120 and alarm system 130 are not involved. Optionally, designing a motion pattern includes evaluation of the neurological impairment and motor deficit of the user, and generation of a motion stereotype that will serve to perform exercise by the user. It should be noted that the motion design for this method differs from motion design for standard rehabilitation programs. In this method the motion pattern does not have to be functionally related to the user's ADL. It would be good if the motion pattern can use for the functional capacity of the ADL, but it is not a necessary condition.

Additionally, it will be good if the motion pattern enables motion of the wheelchair. However, if the type of neurological deficiency of the user does not allow it exercise can be performed when the wheelchair is at rest.

Optionally, the motion pattern is generated to meet the following conditions:

1. Exploit the strength of the large muscles, for example the hip and pelvic arch muscles. These muscles significantly increase the utilization of oxygen by the body.

2. The motion should be comfortable for the patient.

3. The motion pattern allows training for at least 30 minutes.

To accommodate the design of a motion pattern that fits the neurological deficiencies of the user as described above, exercise device 110 includes that:

1. Usage of exercise device 110 provides that the bending angle of the damaged extremity is controlled by the stretching angle of the matching joint (e.g. the other hand or foot that is not damaged). As a result, the patient is able to actively and independently reduce the spastic state of the damaged extremity muscles according to his needs, without assistance of another person, and without exceeding the pain barrier.

2. Usage of exercise device 110 provides that the user may perform passive/active motion of his legs.

3. Usage of exercise device 110 allows a different load to be afflicted on each leg independently.

In an exemplary embodiment of the invention, the physiotherapist visits the user at his or her home after being released from the hospital. Alternatively, the physiotherapist may visit the user at the hospital before being released.

In an exemplary embodiment of the invention, the physiotherapist evaluates the neurological impairments and motor deficiencies of the user, for example by checking the muscles of the user to determine, which muscles are unharmed, which are in a spastic state and which need extra usage, for example to prevent contractures. Optionally, the physiotherapist generates a motion pattern stereotype for the user to perform over and over with exercise device 110, to improve his or her aerobic state.

In an exemplary embodiment of the invention, the physiotherapist may adjust the resistance of the various parts of exercise device 110 so that they will move with greater or weaker resistance based on the needs of the user, for example an impaired limb can be set to move with less resistance than a healthy limb. During this stage only exercise device 110 is used, whereas ergometer 120 and alarm 130 are not required.

In an exemplary embodiment of the invention, after designing the motion pattern (220) for the user, the physiotherapist trains the user to use exercise device 110 while performing the motion pattern.

Once the user is trained to use exercise device 110 the user is required to undergo cardiorespiratory exercise testing to plan a fitness program (230) for the user. The fitness program defines the frequency, the duration and the intensity of the exercise program that the user is required to perform in view of his or her medical situation. In an exemplary embodiment of the invention, planning the fitness program (230) is performed at the medical center 150, since it generally requires equipment, which is only available at stationary medical centers.

In an exemplary embodiment of the invention, during planning of the fitness program (230) the stroke victim is connected to a cardiorespiratory fitness system while performing exercise using exercise device 110. Optionally, the cardiorespiratory fitness system performs an integrative cardiopulmonary exercise test, while the system monitors the stroke victim's physiological parameters, which include:

1. Oxygen consumption ($V'O_2$);
2. Carbon dioxide release ($V'CO_2$);
3. Heart rate (HR);
4. Blood pressure (BP);

and optionally other parameters regarding the physiological state of the stroke victim while performing exercise.

These parameters allow determination of the supply of oxygen to the myocardium, the muscles of locomotion, and the blood stream. Additionally, the rate of release of $CO_2$ from the blood stream can be determined. These parameters allow a practitioner to evaluate the cardiorespiratory fitness of the user while performing the test.

During the testing stage the user performs exercise using exercise device 110 and the readings of ergometer 120 are recorded. Optionally, during the testing the user is requested to perform exercise at various rates so that the practitioner performing the test may plan a fitness program (230) that fits the user, for example to perform the designed motion pattern (220) at a specific rate for a first time period and then perform the designed motion pattern (220) at a different rate for a second time period. Based on the testing the optimal and maximal permissible levels of exercise for the user are determined.

In an exemplary embodiment of the invention, the test protocol is custom designed for each user. Following is an exemplary case dealt with according to an exemplary embodiment of the invention. A 56 year old male is admitted to the medical center 150 with right hemiparesis due to an ischemic left hemispheral cerebral infarction. His history includes one myocardial infarction four years ago. Based on the man's cardiac status, the medical practitioner is concerned with the safety of the man in performing a stroke rehabilitation program. The practitioner prescribes a cardiovascular exercise test to determine if the man can perform an exercise program and to determine the intensity of the program.

The test is performed using exercise device 110. The initial workload is 10 watts, with work rate increments of 10 W every 2 minutes. The practitioner tests the exercise duration until the tolerance limit of the man, During the test the man provides a breath-by-breath analysis of respiratory gas exchange at rest and during a period of exercise, the intensity of which is increased incrementally until symptoms limit testing or the man reaches maximal levels. Information on airflow, O2 consumption, CO2 production, and heart rate are collected and used for computation of other variables. The patient's electrocardiogram and blood pressure are also continuously monitored throughout the test. At the end of the test the man should show volitional fatigue without signs of cardiopulmonary distress.

The results: The resting heart rate, blood pressure and ECG are normal. The ECG shows no dysrhythmia or ischemic change during the test and cool-down. Breathing reserve (BR), Breathing equivalents (EQO2, EQCO2) and Dead space ventilation (VD/VT) during the test are normal.

The heard rate achieved is low at 130 beats per minute (quite high for the level of exertion, but consistent with severe deconditioning). The pressure response is normal during and after the test. The Maximum oxygen uptake (peak VO2) is 21 ml/min/kg at the work rate 60 watts.

Interpretation: The results indicate that the man can safely participates in a training program .The test demonstrated, however, that he is deconditioned.

Guide prescription of exercise: Optimally work loading should by at 50% of the maximal work rate achieved during the test. Optimally work loading for this patient is 30 watts. Maximally work loading should by at 70% of the maximal work rate achieved during the test. Maximally work loading for this patient is 45 watts. In other words, the range for alarm system calibration should by from 30 watts up to 45 watts.

It should be noted that the test is performed using exercise device 110 and the training program will likewise be performed using the same exercise device 110. Additionally the motion pattern used is the same for the test and for the exercise program.

Ergometer 120 does not directly measure the metabolism of the user that represents the user's ability to benefit from the exercise being performed, since:

1. Ergometer 120 provides a measure proportional to the amount of work performed with the device, although some of the work is wasted on heat or other forms that are not measurable by ergometer 120.

2. Each person responds differently to the performance of exercise depending on their physiological status.

In an exemplary embodiment of the invention, the cardiopulmonary exercise test provides a global assessment of the user's responses to exercise, wherein the responses involve the pulmonary, cardiovascular, hematopoietic, neuropsychological and skeletal muscle systems. These parameters are used together with the readings of ergometer 120 to be able to determine the user's state when performing exercise with exercise device 110 responsive to readings from ergometer 120 alone.

Based on the findings of the testing stage, a trained practitioner (e.g. a doctor, nurse or medical technician) can then program (240) alarm system 130 of exercise device 110 to provide indications to the user, to let him/her know what state they are in while performing exercise, for example if they are correctly performing the planned fitness program (230) and if they are performing at the required rate or if they are exceeding the required rate. Optionally, if the user does not follow the plan or if the user reaches an abnormal rate, alarm system 130 will provide an indication so that the user will know to correct the performance and/or reduce or increase the rate and/or cease doing exercise.

In an exemplary embodiment of the invention, alarm system 130 is a programmable circuit and is programmed to provide an output as feedback to the user, for example as a visual signal and/or as an audio signal. Optionally, the feedback may be verbal messages, music, continuous beeping at different rates or other audio signals. Likewise the visual signal may be actual numeric values, an analog numerical display, flashing lights at specific rates or other visual signals. Optionally, the feedback helps the user to stick to the planned fitness program and/or to a desired motion.

In some embodiments of the invention, alarm system 130 may provide feedback to exercise device 110 in addition or instead of to the user, for example when alarm system 130 detects that the user has deviated from the plan or has exceeded his/her recommended rate the alarm system 130 will serve as an electronic lock, for example by instructing exercise device 110 to shut down to prevent the user from getting hurt, for example from sudden cardiac death. Alternatively, alarm system 130 may cause exercise device 110 to increase the resistance to the user's motion so that the user will be forced to stop. In some embodiments of the invention, alarm 130 is programmed to keep track of the usage of exercise device 110 and remind the user to perform exercise periodically.

After preparing the plan (230) and programming (240) alarm system 130 the user is sent home with exercise device 110 to perform (250) the self care rehabilitation plan. In some embodiments of the invention, alarm system 130 keeps track of the performance of the user so that a practitioner may review the user's progress. Optionally, method 200 is repeated as needed based on the progress of the user.

In some embodiments of the invention, alarm system 130 is connected over a communication network (e.g. the Internet) to medical center 150, so that medical center 150 can keep track of the progress of the user. In some embodiments of the invention, the user wears other measurement devices while performing exercise with exercise device 110, for example to provide Holter or ECG data, so that medical center 150 receives additional physiological data in addition to the data from ergometer 120. Optionally, only authorized personnel from medical center 150 may change the programming of alarm system 130. In some embodiments of the invention, the programming can be changed by commands sent over the communication network, so that the user does not have to go to the medical center to have the programming of alarm system 130 changed or repaired.

Optionally, the benefits of apparatus 100 include:
1. That the user can perform an exercise training program in the comfort of his or her own home without traveling;
2. That no human assistance is generally required for the user to perform the rehabilitation exercise plan;
3. That the user is monitored and receives automatic feedback to exercise at a pre-designated level of effort and to prevent over exercising.

Generally, stroke victims suffer from impairments to the smaller muscles; larger muscles such as the pelvic proximal muscles are generally not impaired. Additionally, exercising the smaller muscles tends to have less effect on the supply of oxygen to the blood system relative to exercising the larger muscles. In an exemplary embodiment of the invention, the pelvic proximal muscles of the thigh are used to perform exercise with exercise device 110, since most stroke victims are able to activate these muscles and they contribute strongly to improving the aerobic system of the user. Alternatively or additionally, other muscles may be used by designing exercise device 110 to cater to stroke victims with various impairments as explained below. In an exemplary embodiment of the invention, performing exercise with exercise device 110 will increase muscle strength and prevent various problems. Typically 4 common problems are dealt with when using standard rehabilitation procedures:

1. Muscles that are in a spastic state need to be softened by exercising them to prevent the development of pathological walking models and contractures;
2. Muscles with a low amplitude of junction motion need to be stretched to prevent the development of contractures;
3. The development of contractures lead to the feeling of pain when using the muscles involved; and
4. Pathological walking models and limb motion are preserved due to lack of use and exercising of the muscles.

In an exemplary embodiment of the invention, the above issues are taken into consideration in the design of exercise device 110.

Figure 3:
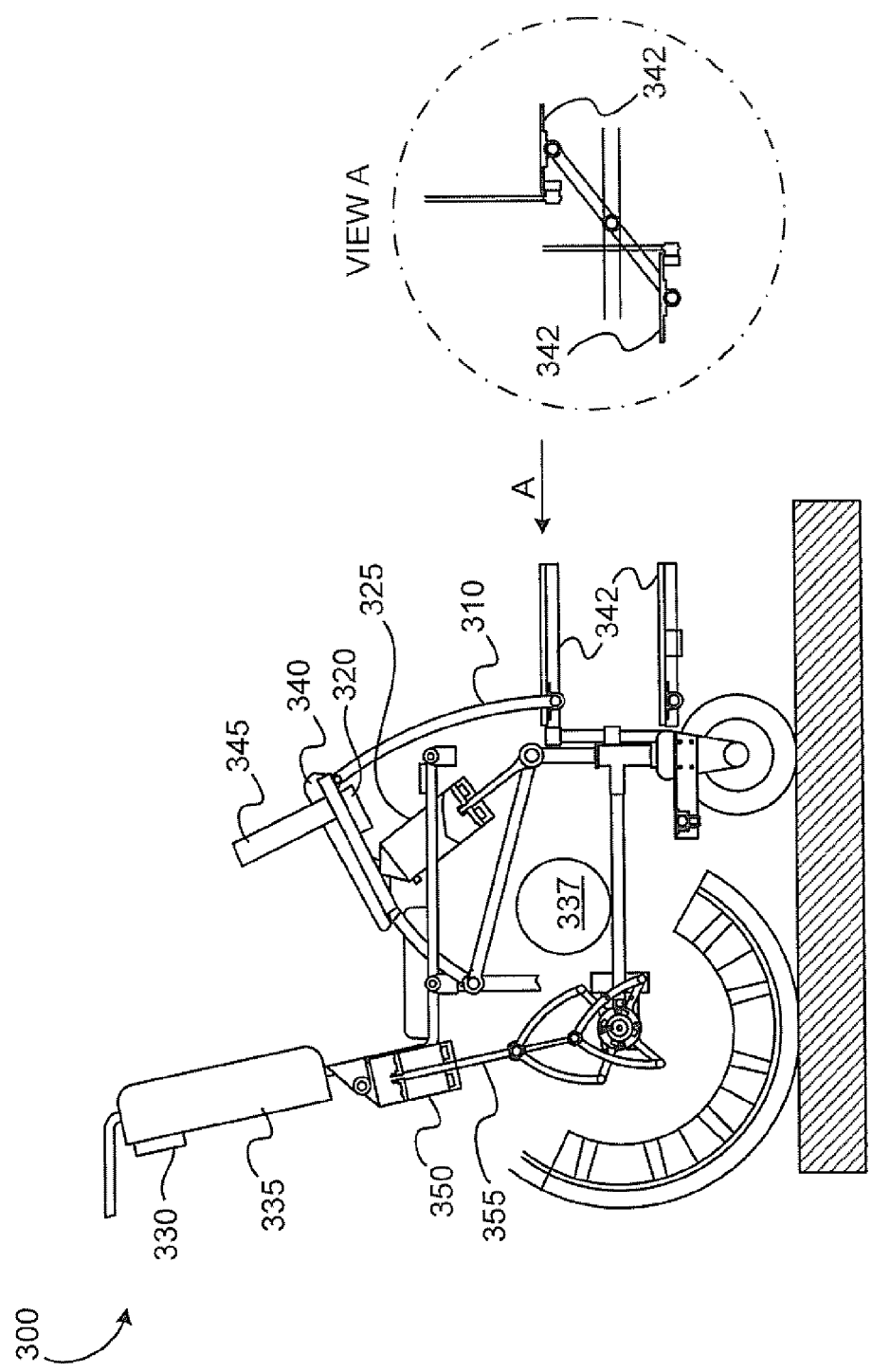
FIG. 3 is a schematic illustration of a side view of an apparatus for performing rehabilitation exercise installed on a wheel chair, according to an exemplary embodiment of the invention.

FIG. 3 is a schematic illustration of a side view of an apparatus 300 for performing rehabilitation exercise deployed on a wheel chair, according to an exemplary embodiment of the invention. In an exemplary embodiment of the invention, apparatus 300 includes an exercise device 310, an ergometer 320 and an alarm system 330. Optionally, alarm system 330 may be deployed in a common encasement with ergometer 320 instead of in separate encasements as shown in FIG. 3. In an exemplary embodiment of the invention, exercise device 310 is designed to have two symmetrical pads 340 to be placed under the thighs of the user and strapped onto the user's thighs with a strap 345 optionally, pads 340 are connected to two pedals 342 that are connected reciprocally (as shown in view A), so that when a user raises one thigh-leg the other thigh-leg goes down and vice versa. Optionally the reciprocal motion helps to retrain the user to control his/her muscles and not maintain a pathological walking model that is common to stroke victims.

In an exemplary embodiment of the invention, a pump 325 is positioned under each pad 340, so that the reciprocal motion of the user's thighs fills up a compressed air reservoir 335 while the user is performing exercise. In some embodiments of the invention, the resistance of each pump 325 can be adjusted, for example by enlarging or reducing the size of the air outlet of the pump to control the force required to move each pad 340. Thus a physiotherapist can adjust the resistance of pad 340 when training the user to use exercise device 310. In an exemplary embodiment of the invention, ergometer 320 records the work performed by the user by monitoring pads 340. Optionally, the readings are updated with the resistance settings of each pump 325 so that it can correctly record the amount of work performed by the user, for example if pumps 325 are set with low resistance then the user will perform less work than if the pumps are set with a high resistance. Optionally, each pump may be set to a different degree of resistance depending on the physical ability of the user, for example if the user is unable to control one leg the resistance of the pump will be set to the minimum for that leg.

In an exemplary embodiment of the invention, the maximum height of raising pad 340 and angle of lifting can also be adjusted to allow a greater or lesser motion span depending on the user's size and condition. Optionally, ergometer 320 records the movements of pads 340 taking into account the adjustments made to accommodate for the specific user. Ergometer 320 provides alarm system 330 with its measurement. In some embodiments of the invention, alarm system 330 may provide a continuous output related to the amount of work or rate of work performed by the user. Optionally, alarm system 330 may provide a visual output or audio output to relay these values. The visual output may include a display (e.g. LCD) or row of lights (e.g. Led's) and the audio output may include creating a steady beeping or other sounds. Optionally, if the user exceeds the predetermined amount of work or rate of worked allowed during an exercise session alarm system 330 may give off a loud signal and/or flash lights to warn the user. In some embodiments of the invention, alarm system 330 may instruct ergometer 320 to prevent pads 340 from moving, for example by increasing the resistance.

In some embodiments of the invention, a container of compressed air 337 that is loaded from an external source, for example by an electric pump, is used to assist in moving the user's thighs/legs. Optionally, the air from container 337 is provided intermittently to one or both of pumps 325 to help lift the user's legs in a case that the user cannot move one or both of his thigh muscles by his self or with the aid of the other leg.

In some embodiments of the invention, exercise device 310 is used to perform exercise while the wheel chair is stationary. Alternatively or additionally, exercise device 310 may be used to move the wheel chair. In an exemplary embodiment of the invention, the compressed air provided by pumps 325 to reservoir 335 is used to move the wheel chair, either while performing exercise or after performing exercise and loading reservoir 335.

Figure 4:
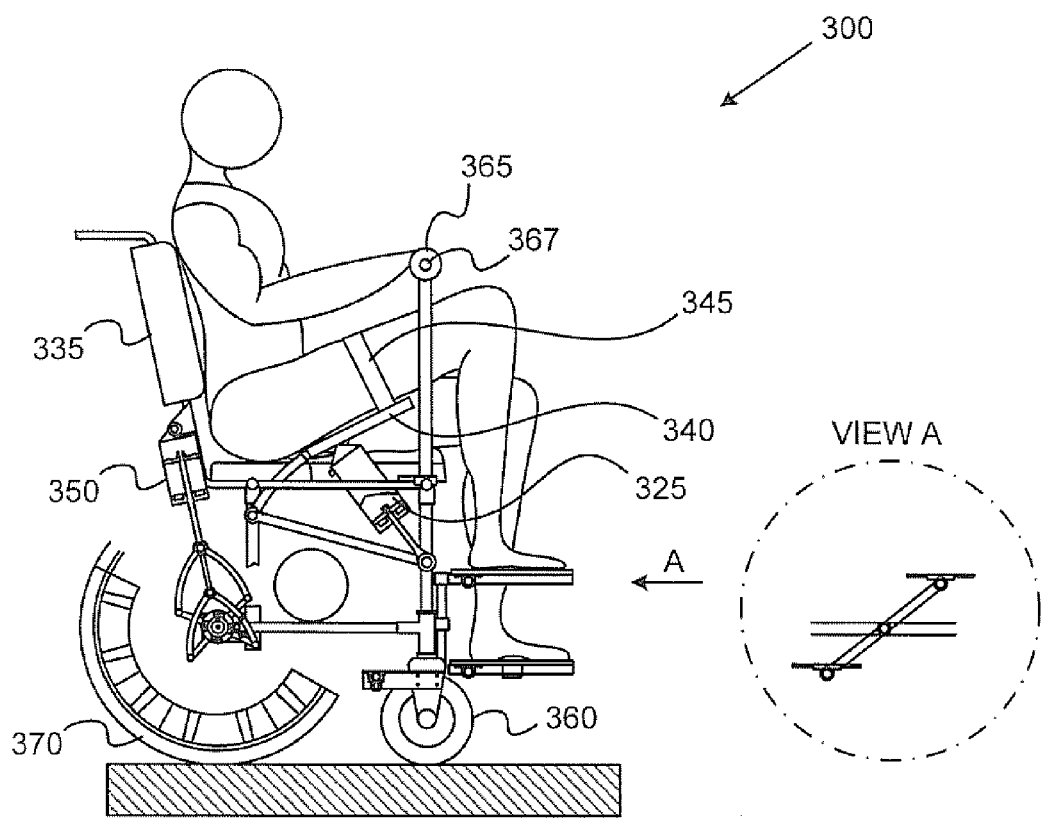
FIG. 4 is a schematic illustration of a side view and top view of an apparatus for performing rehabilitation exercise, according to an exemplary embodiment of the invention.
Figure 4:
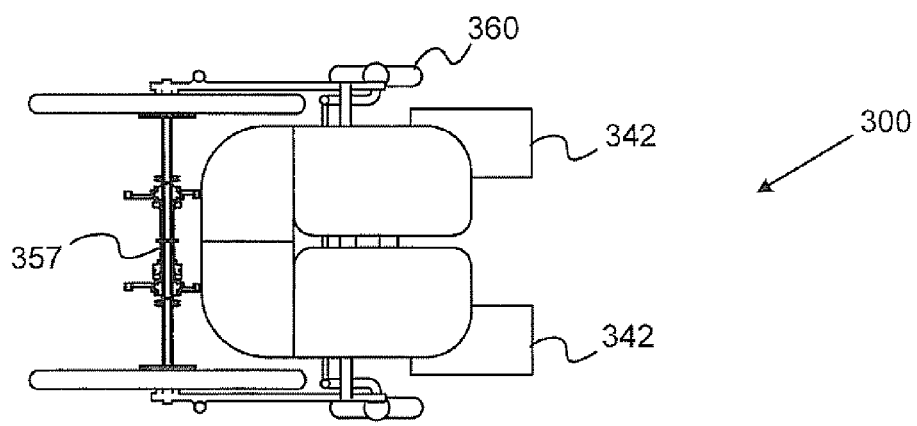

FIG. 4 is a schematic illustration of a side view and top view of apparatus 300 for performing rehabilitation exercise, according to an exemplary embodiment of the invention. In an exemplary embodiment of the invention, the user pumps air into reservoir 335 while performing exercise. The compressed air is then used to activate one or more (e.g. 2) power cylinders 350 that each push a rod 355 up and down. The up and down motion of rods 355 is transferred to a switching mechanism 357 that converts the motion of rods 355 to forward and/or backward motion of main wheels 370 of the wheel chair. Optionally, front wheels 360 serve to steer the wheel chair as it moves forward or backward. In an exemplary embodiment of the invention, the user grasps a steering rod 365 to control the direction of front wheels 360. Alternatively, the user may move the wheel chair in the standard way by grasping the main wheels 370 with his hands directly.

In some embodiments of the invention, the user places straps 345 over his hands or grasps them with his hands to use his hands to aid in lifting and lowering his legs. This option allows the use of the hands in performing exercise, especially if the user has problems with performing the exercise using only his legs.

In some embodiments of the invention, switches 367 on steering rod 365 are provided to control the speed and direction (forward/backward) of motion of the wheel chair. Optionally, steering rod 365 is also used to break the motion in case of emergency, for example by pressing down on steering rod 365.

Figure 5:
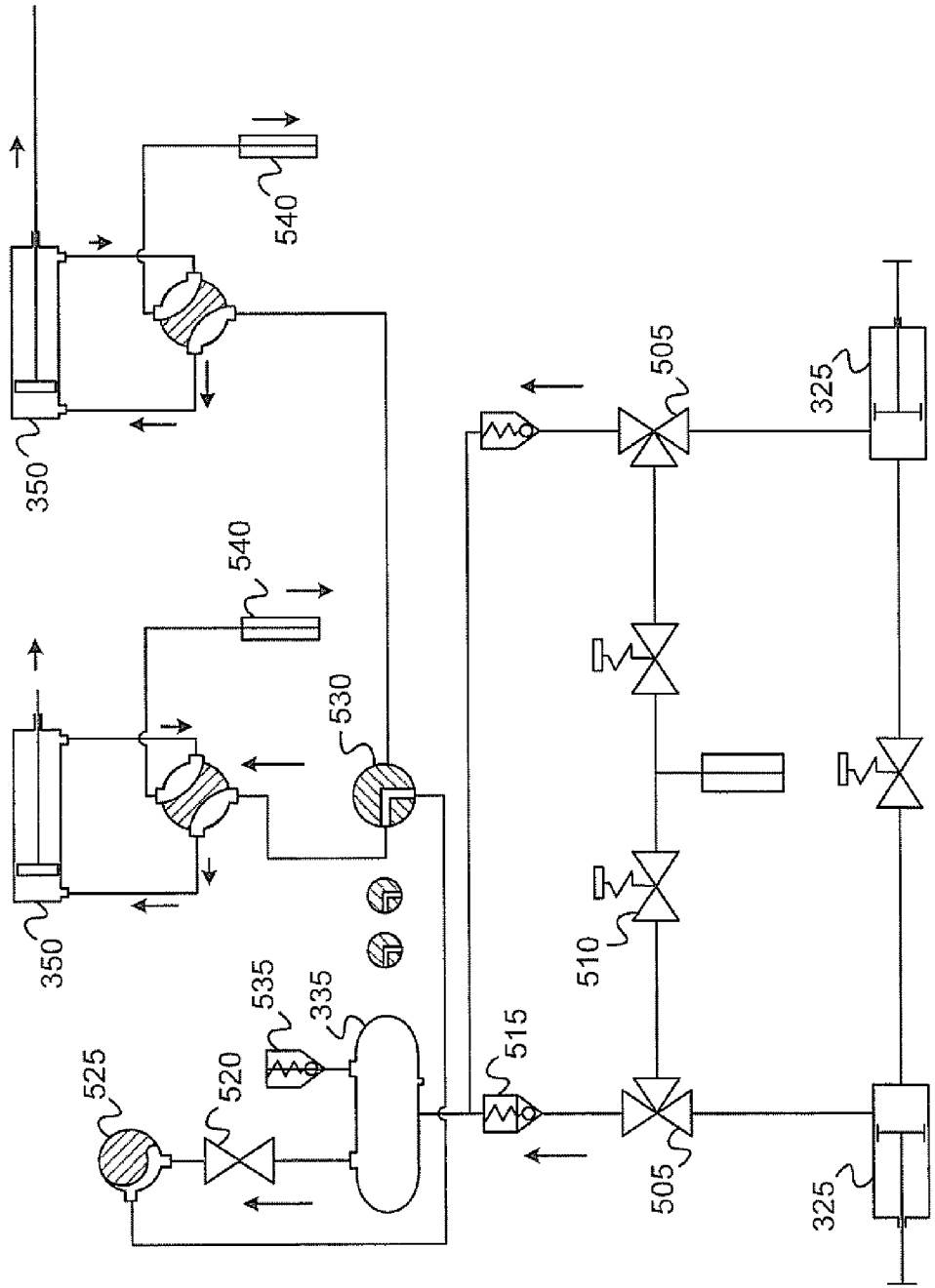
FIG. 5 is a schematic illustration of a pneumatic system for the operation of an apparatus for performing rehabilitation exercise, according to an exemplary embodiment of the invention.

FIG. 5 is a schematic illustration of a pneumatic system 500 for the operation of apparatus 300 for performing rehabilitation exercise, according to an exemplary embodiment of the invention.

In an exemplary embodiment of the invention, pneumatic system 500 shows a standard controllable transfer system of compressed air from pumps 325 to reservoir 335, and from reservoir 335 to power cylinders 350. the pneumatic system 500 include splitters 505, inverse valves 510, expansion valves 515, cut off valves 520, a speed control valve 525, a switch valve 530, safety valves 535, mufflers 540 and other elements as is known in the art.

Figure 6:
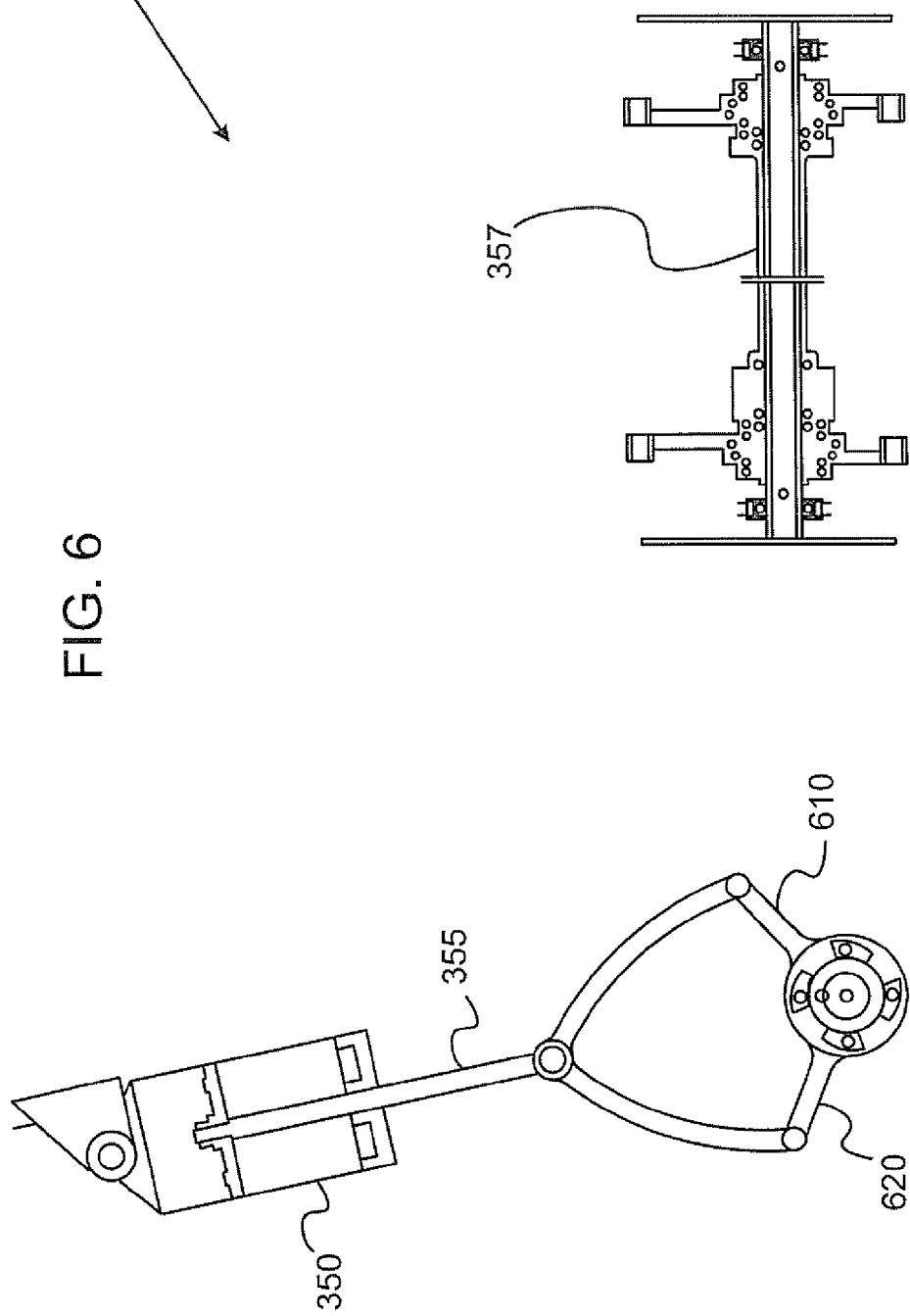
FIG. 6 is a schematic illustration of a switching system for the operation of an apparatus for performing rehabilitation exercise, according to an exemplary embodiment of the invention.

FIG. 6 is a schematic illustration of a mechanical switching system 600 for the operation of apparatus 300 for performing rehabilitation exercise, according to an exemplary embodiment of the invention.

In an exemplary embodiment of the invention, when rod 355 moves up or down it pushes arm 610 and arm 620, one rotates clockwise and the other rotates counter clockwise. Optionally, switching mechanism 357 is a standard switching gear and clutch system that enables capturing the rotational motion caused by arm 610 and 620 to turn the main wheel 370 of the wheel chair in the direction desired by the user responsive to switches 367 on steering rod 365.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

I claim:

1. A transportable apparatus for performing cardiovascular training for stroke survivors, comprising:
an exercise device that is adapted to enable a user to perform a specific motion pattern based on motor deficiencies of the user, by adjusting the device to allow performance of the specific motion pattern; wherein the device adjustments enable the device to perform reciprocal motion by moving a damaged limb responsive to motion of a healthy limb; wherein said exercise device is transportable by a single person so that it may be transported and used at the user's home;
an ergometer that provides an indication of the amount of effort exerted by the user of the exercise device;
an alarm system that provides an indication to the user responsive to the readings of the ergometer;
wherein said exercise device is configurable to function in a test mode and in an exercise mode;
Wherein in the test mode the user performs a cardiorespiratory exercise test with said exercise device after being configured to perform the specific motion pattern, and the readings of the ergometer are recorded; and
wherein the recorded readings of the ergometer are used to preprogram said alarm system to provide indications responsive to one or more readings of the ergometer for the specific user when using the device in the exercise mode to perform the specific motion pattern.

2. An apparatus according to claim 1, wherein said exercise device is adapted to be attached to a wheel chair to enable performing exercise while seated in the wheel chair.

3. An apparatus according to claim 1, wherein said alarm system provides continuous readings related to the amount of effort performed by the user.

4. An apparatus according to claim 3, wherein said readings are provided as audio signals.

5. An apparatus according to claim 3, wherein said readings are provided as visual signals.

6. An apparatus according to claim 1, wherein the exercise device can be adjusted to have a higher or lower level of resistance to the motion performed by the user, so that the level of resistance matches the ability of the user.

7. An apparatus according to claim 6, wherein the exercise device is calibrated with a different level of resistance on each side of the exercise device.

8. An apparatus according to claim 1, wherein the cardiorespiratory exercise test determines a maximum amount of effort allowed by the user during a single session.

9. An apparatus according to claim 1, wherein said alarm system provides signals to remind the user to perform exercise.

10. An apparatus according to claim 1, wherein said alarm system provides signals to notify the user to stop performing exercise.

11. An apparatus according to claim 1, wherein said alarm system provides signals to help the user to follow a pre-programmed exercise plan.

12. An apparatus according to claim 1, wherein said alarm system prevents the user from continuing to perform exercise with the exercise device.

13. An apparatus according to claim 2, wherein said exercise device is adapted to be used while the wheel chair is stationary.

14. An apparatus according to claim 2, wherein said exercise device is adapted to enable the user to control the motion of the wheel chair.

15. An apparatus according to claim 2, further comprising a pump that produces compressed air from the exercise performed by the user.

16. An apparatus according to claim 15, wherein the compressed air is used to move the wheel chair forward or backward, instead of moving the wheel chair by hand.

17. An apparatus according to claim 1, wherein compressed air stored in a container in the exercise device is provided to a pump to perform the reciprocal motion by moving the user's damaged limb responsive to motion of the healthy limb.

18. A method of performing home based cardiovascular exercise training for stroke survivors, comprising:

designing a specific motion pattern to be performed by a user of a transportable exercise device based on motor deficiencies of the user;

adjusting the exercise device based on the motor deficiencies of the user to allow performance of the specific motion pattern; wherein the adjustments enable the device to perform reciprocal motion by moving a damaged limb responsive to motion of a healthy limb;

training the user to use the exercise device;

testing the cardiorespiratory ability of the user while using the exercise device after being adjusted to allow performance of the specific motion pattern and monitoring the readings of an ergometer that provides indication of the effort of the user while using the device;

planning a fitness program based on the testing;

using the results of said testing to program an alarm system of the exercise device to provide the user with indications responsive to various readings of the ergometer while using the exercise device.

19. A method according to claim 18, wherein said exercise device is adapted to be attached to a wheelchair.

20. A method according to claim 18, further comprising warning the user if he exceeds a pre-determined exercise rate.

21. A method according to claim 18, wherein said alarm system prevents said user from performing exercise with said exercise device responsive to readings from the ergometer.

* * * * *